US00PP26065P2

(12) United States Plant Patent
Li

(10) Patent No.: US PP26,065 P2
(45) Date of Patent: Nov. 10, 2015

(54) ***VERBENA* PLANT NAMED 'KLEVP12430'**

(50) Latin Name: ***Verbena* sp.**
Varietal Denomination: KLEVP12430

(71) Applicant: Klemm+Sohn GmbH & Co. KG, Stuttgart (DE)

(72) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 23 days.

(21) Appl. No.: 14/120,221

(22) Filed: May 7, 2014

(51) Int. Cl.
*A01H 5/02* (2006.01)

(52) U.S. Cl.
USPC ..... Plt./308

(58) Field of Classification Search
USPC ..... Plt./308
CPC ..... A01H 5/02; A01H 5/00
See application file for complete search history.

*Primary Examiner* — Kent L Bell
(74) *Attorney, Agent, or Firm* — Barbara Campbell; James M. Weatherly; Cochran Freund & Young, LLC

(57) ABSTRACT

A new *Verbena* plant particularly distinguished by large, pink flowers with white centers, an upright plant habit, good tolerance to powdery mildew, and early flowering, is disclosed.

1 Drawing Sheet

Genus and species: *Verbena* sp.
Variety denomination: 'KLEVP12430'.

BACKGROUND OF THE NEW PLANT

The present invention comprises a new and distinct variety of *Verbena,* botanically known as *Verbena* sp., and hereinafter referred to by the variety name 'KLEVP12430'. 'KLEVP12430' originated from a cross-pollination conducted in April 2009 in Sydney, Australia between the proprietary female *Verbena* variety 'U 9107' (unpatented), and the proprietary male *Verbena* variety '1F2/V740' (unpatented).

The seeds from the cross were sown and plants were grown for evaluation, where an individual plant designated 'KLEVP12430' was selected from the group of plants in Cobitty, NSW, Australia in September 2010.

In September 2010 'KLEVP12430' was first vegetatively propagated by vegetative cuttings in Cobitty, NSW, Australia. 'KLEVP12430' was found to reproduce true to type in successive generations of asexual propagation via vegetative cuttings.

CROSS-REFERENCE TO RELATED APPLICATIONS

A Canadian Plant Breeders Rights application was filed on Feb. 25, 2014, application number 14-8205. 'KLEVP12430' has not been sold or made publicly available more than one year prior to the filing date of the present application.

SUMMARY

The following are the most outstanding and distinguishing characteristics of this new variety when grown under normal horticultural practices in Stuttgart, Germany.

1. Large, pink flowers with white centers;
2. An upright plant habit;
3. Good tolerance to powdery mildew; and
4. Early flowering.

DESCRIPTION OF THE PHOTOGRAPH

This new *Verbena* plant is illustrated by the accompanying photograph which shows the plant's overall plant habit including form, foliage, and flowers.

The photograph is of a two to three-month old plant grown in a greenhouse in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLEVP12430'. The data which define these characteristics were collected from asexual reproductions carried out in Stuttgart, Germany. Data was collected on three-month-old plants grown in a greenhouse in Stuttgart, Germany in February 2014. Color references are to The R.H.S. Colour Chart of The Royal Horticultural Society of London (R.H.S.), 2005.

Classification:
- *Family*.—Verbenaceae.
- *Botanical*.—*Verbena* sp.
- *Common*.—*Verbena*.
- *Designation*.—'KLEVP12430'.

Parentage:
- *Female parent*.—The proprietary female *verbena* variety 'U 9107' (unpatented).
- *Male parent*.—The proprietary male *verbena* variety '1F2/V740' (unpatented).

Plant:
- *Growth and branching habit*.—Upright.
- *Height* (*from top of soil*).—30.0 cm.
- *Width* (*horizontal plant diameter*).—30.0 cm.
- *Time to produce a finished flowering plant*.—Approximately 8 weeks.
- *Time to initiate and develop roots*.—3 weeks.
- *Root description*.—White.

Stems:
*Number of branches per plant*.—More than 10.
*Growth habit*.—Semi-upright.
*Length*.—20.0 cm.
*Diameter*.—1.0 cm.
*Internode length*.—Approximately 2.0 cm.
*Color*.—RHS 130D.
*Anthocyanin*.—Absent.
*Texture and appearance*.—Pubescence, round.

Leaves:
*Arrangement*.—Opposite.
*Immature and mature leaf color*.—Upper surface: RHS 141A. Lower surface: RHS 141C.
*Length*.—2.5 cm.
*Width*.—1.5 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D.
*Petioles*.—Length: 1.0 cm. Diameter: 0.1 cm. Color: RHS 141D. Texture: Leathery.

Flower buds:
*Shape*.—Tall, cylindrical.
*Length*.—0.5 cm.
*Diameter*.—0.1 cm.
*Color* (*at tight bud*).—RHS 75C.

Inflorescence:
*Blooming habit* (*flowering season*).—Continuously.
*Lastingness of individual blooms on the plant*.—2 weeks.
*Fragrance*.—Absent.
*Inflorescence type*.—Umbel.
*Length of inflorescence*.—6.0 cm.
*Diameter of inflorescence*.—6.0 cm.
*Number of florets per inflorescence*.—More than 15.
*Peduncle*.—Color: RHS 141A. Length: 4.0 cm. Diameter: 0.1 cm.

Florets:
*Length*.—2.0 cm.
*Diameter*.—4.0 cm.
*Texture*.—Glossy.
*Form*.—Umbel.
*Length*.—0.1 cm.
*Diameter*.—4.0 cm.
*Color*.—Immature: Upper surface: RHS 75A. Lower surface: RHS 75B. Mature: Upper surface: RHS 75B. Lower surface: RHS 75C.
*Corolla tube length*.—0.2 cm.
*Corolla tube color*.—RHS 75C.
*Petals*.—Length of lobe: 2.0 cm. Diameter of lobe: 2.0 cm. Lobe shape: Round. Apex: Acute. Base: Obtuse. Margin: Entire. Texture (both upper and lower surfaces): Glossy, satiny.
*Pedicels*.—Length: 2.0 cm. Diameter: About 0.1 cm. Color: RHS 75A. Texture and appearance: Hairy, dull. Arrangement: Round.

Sepals:
*Shape*.—Lanceolate.
*Apex*.—Acute.
*Base*.—Obtuse.
*Margin*.—Entire.
*Length*.—2.0 cm.
*Diameter*.—0.5 cm.
*Color*.—RHS 141C.
*Texture* (*both upper and lower surfaces*).—Hairy, dull.

Reproductive organs:
*Stamens*.—Present.
*Quantity*.—Numerous.
*Filament length*.—0.1 cm.
*Filament diameter*.—Less than 0.1 cm.
*Anther*.—Shape: Elliptic. Color: RHS 141D. Length: Less than 0.1 cm. Diameter: Less than 0.1 cm.
*Pollen amount*.—Absent.
*Pistils*.—Number: 1. Length: 1.0 cm. Diameter: Less than 0.1 cm. Stigma: Color: RHS 141D. Appearance: Ovate. Length: Less than 0.1 cm. Diameter: Less than 0.1 cm. Style: Color: RHS 141D. Length: 0.2 cm. Diameter: Less than 0.1 cm. Appearance: Long.

Fruit and seed set: None observed.

Disease and pest/insect resistance: Good resistance to powdery mildew.

COMPARISON WITH PARENTAL LINES AND KNOWN VARIETY

'KLEVP12430' is distinguished from its parents as described in Table 1.

TABLE 1

Comparison with Parental Lines

| Characteristic | Variety 'KLEVP12430' | Female parent 'U 9107' | Male Parent '1F2N740' |
|---|---|---|---|
| Flower richness | Good | Low | Good |
| Earliness | Early | Late | Medium |

'KLEVP12430' is most similar to the commercial *Verbena* 'Empress Pink' (patent status unknown). Differences between the varieties are described in Table 2.

TABLE 2

Comparison with Similar Variety

| Characteristic | Variety 'KLEVP12430' | Commercial line 'Empress Pink' |
|---|---|---|
| Resistance to powdery mildew | Very good - better than 'Empress Pink' | Good but not as good as 'KLEVP12430' |
| Flower size | Bigger than 'Empress Pink' | Smaller than 'KLEVP12430' |

I claim:

1. A new and distinct variety of *Verbena* plant designated 'KLEVP12430' as shown and described herein.

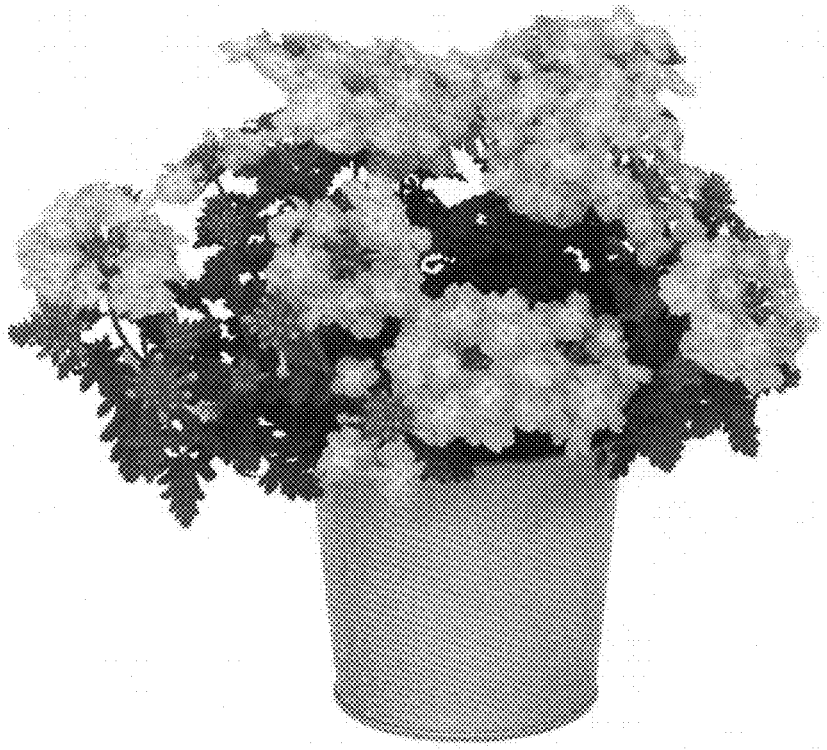

* * * * *